US006185448B1

(12) United States Patent
Borovsky (10) Patent No.: US 6,185,448 B1
(45) Date of Patent: Feb. 6, 2001

(54) APPARATUS AND METHOD FOR LOCATING AND MAPPING A CATHETER IN INTRACARDIAC OPERATIONS

(76) Inventor: Simcha Borovsky, 17-25 Hunter Pl., Fair Lawn, NJ (US) 07410

( * ) Notice: Under 35 U.S.C. 154(b), the term of this patent shall be extended for 0 days.

(21) Appl. No.: 09/163,270

(22) Filed: Sep. 29, 1998

(51) Int. Cl.$^7$ ....................................................... A61B 5/05
(52) U.S. Cl. .......................... 600/424; 600/431; 600/481; 600/508; 606/27; 606/28; 606/29; 606/30; 606/31; 606/130; 607/2; 607/3; 607/96; 607/122
(58) Field of Search ............................. 607/2, 3, 96, 122; 600/373, 374, 409, 407, 424, 431, 481, 508, 585, 9, 10, 11, 12, 13; 606/130, 27, 28, 29, 30, 31

(56) References Cited

U.S. PATENT DOCUMENTS

| 5,425,367 | 6/1995 | Shapiro et al. . | |
|---|---|---|---|
| 5,480,422 | 1/1996 | Ben-Haim . | |
| 5,558,091 | * 9/1996 | Acker et al. | 600/424 |
| 5,592,939 | * 1/1997 | Martinelli | 128/653.1 |
| 5,697,377 | 12/1997 | Wittkampf . | |
| 5,711,299 | * 1/1998 | Manwaring et al. | 600/417 |
| 5,727,553 | 3/1998 | Saad . | |
| 5,738,096 | 4/1998 | Ben-Haim . | |
| 5,752,513 | 5/1998 | Acker et al. . | |
| 5,769,843 | * 6/1998 | Abela et al. | 606/10 |
| 5,928,248 | * 7/1999 | Acker | 606/108 |

OTHER PUBLICATIONS

Claus Schmitt et al, "Low Energy Intracardiac Cardioversion after Failed Conventional External Cardioversion of Atrial Fibrillation," *Journal of the American College of Cardiology, JACC,* vol. 28, No. 4, Oct., 1996, pp. 994–999.

Hall Generators—brochure by F.W. Bell, a division of Bell Technologies Inc., Orlando, FL, Jan., 1997.

NVE (Nonvolatile Electronics, Inc.) , Eden Prairie, MN, brochure (undated).

* cited by examiner

*Primary Examiner*—Marvin M. Lateef
*Assistant Examiner*—Jeoyuh Lin (57) ABSTRACT

An apparatus for locating and mapping a catheter in a heart invasive operation, includes a permanent magnet with a north pole face, a permanent magnet with a south pole face, a frame for positioning the magnets on opposite sides of a person's body; first and second motors for revolving the permanent magnets in synchronism and in alignment with each other to create a directional magnetic field that revolves 360 degrees through the person's heart; a catheter for insertion into the heart, the catheter including a first sensor group of three mutually orthogonal sensors at the tip thereof and a second sensor group of three mutually orthogonal sensors in axially spaced relation to the first sensor group, each for detecting the relative strength of the revolving magnetic field; a magnetic field position detector which detects the angular position and speed of movement of the directional magnetic field; a plurality of electrodes spaced along an outer wall thereof for detecting electric signals which run along a wall of the heart; an ablation member at a tip of the catheter for burning out a wall of the heart; and a central processing unit for determining a location of the catheter position in relation to the heart in response to the detected strength of the revolving magnetic field by the first and second sensor groups and the angular position and speed of movement of the directional magnetic field.

20 Claims, 5 Drawing Sheets

APPARATUS AND METHOD FOR LOCATING AND MAPPING A CATHETER IN INTRACARDIAC OPERATIONS

BACKGROUND OF THE INVENTION

The present invention relates generally to an apparatus and method for locating an electrode position, and more particularly, is directed to an apparatus and method for locating and mapping a catheter for use in intracardiac applications such as cardiac arrhythmia, ventricular tachycardia and other heart disorders.

Cardiac arrhythmia, which is an irregular heartbeat, is the leading cause of death in the United States. For example, ventricular tachycardia (VT), which is an excessively fast heartbeat, that is, a very rapid contraction of the heart muscle, is the cause death of about 300,000 patients annually. Therefore, it is necessary to detect defects in the heart rhythm, and locate the position of the these defects.

Generally, with regard to the heart pulses, there is an electrical signal that travels down the inner walls of the heart, contracting the heart from the top to the bottom in much like a squeezing action. As the electrical signal passes vertically along the inner walls of the heart to produce the contraction, the heart then expands again. At the end of the signal, that is, at the bottom of the heart, the signal has ended and a new signal starts at the top of the heart to again begin contraction.

However, oftentimes, there are dead or defective tissue or small lesions on the inner walls of the heart. In such case, the small lesions disturb the conduction of the electrical pulse. This results in delay of the pulse to reach the bottom of the heart and to be entirely canceled out. As a result, an extra pulse is produced which causes the heart to pre-contract again before it should, resulting in a double pulse, or double contraction, causing ventricular tachycardia (VT) or an excessively fast heartbeat. Since a full heart pump is not produced for each pulse, this causes problems in getting the necessary blood flow to all parts of the body.

In order to cure this problem, the defective tissue or small lesions of the heart wall are burned out or ablated. As a result, the burned out areas are bypassed by the electrical signal that travels down the heart wall, so that no double pulse or double contraction is produced, and a regular heartbeat is achieved.

In order to detect this defective tissue of the heart, catheters are conventionally inserted through main blood vessels into the inside of the heart. The catheters have spaced metal contacts on the outside thereof which touch the inner wall of the heart at different locations. When the catheter touches the inner wall of the heart, it detects the signals which stimulate the contraction and which run along the heart. Alternatively, stimulus signals can be supplied to the heart, and be detected by the catheter electrodes. A plurality of such catheters can be provided for such measurement in the heart at one time.

Conventionally, however, this process has proved to be time-consuming, and burdensome with difficulties to locate the electrode position in relation to the heart interior. The procedure for locating the defective tissues utilizes electrophysiology examination that provides mapping by electrical activity of the heart. Specifically, this procedure requires constant movement of the sensing electrodes, combined with x-ray illumination needed for gathering positioning reference points. Such procedure is tedious, time-consuming, and requires constant use of x-ray illumination for imaging and mapping, exposing the patient and physician to high doses of harmful radiation.

Further, locating the position of a catheter inserted into body organs, and in particular, sensitive organs such as the heart, is considered a difficult procedure. The only effective method today is the use of x-ray illumination, as discussed above. However, the x-ray illuminations usually result in poor or fuzzy imaging due to the fact that x-ray does not produce good image of soft tissue in comparison to hard tissue such as bones. Therefore, this procedure results in a poor image of the heart anatomy. In intracardiac mapping applications where accurate positioning of the inserted electrode is important, x-rays therefore do not provide absolute positioning in respect to the heart interior walls.

After mapping the position of the defective tissue or small lesions of the heart, a separate ablation catheter is inserted into the heart and includes a heating element to burn out the defective tissue. Because it is impossible with the use of x-rays to determine the exact location of the defective tissue, the ablation catheter is used to burn out an area which is much larger than each area of defective tissue, in order to ensure that all of the defective tissue is burned out.

This procedure causes problems, because there are key nerves lining the heart, and it is not known from the mere use of the above sensing electrodes if one of the key nerves is being burned out. If it is burned out, the patient may thereafter require a pacemaker.

Thus, with this prior procedure using x-rays, there is no way to determine the exact location of the sensing electrodes or catheters, and there is no way to document previous positions of the catheters. Further, this procedure is long and tedious, and subjects the patient to long use of x-rays, as discussed above.

A summary of this known system and the disadvantages thereof are found at columns 1 and 2 of the U.S. Pat. No. 5,480,422 to Ben-Haim.

OBJECTS AND SUMMARY OF THE INVENTION

Accordingly, it is an object of the present invention to provide an apparatus and method for locating and mapping a catheter position in intracardiac operations that overcomes the aforementioned problems in the prior art.

It is another object of the present invention to provide an apparatus and method for locating and mapping a catheter in intracardiac operations by applying a magnetic field across the heart latitude, and detecting and quantifying this magnetic field with a magnetic sensor device.

It is still another object of the present invention to provide an apparatus and method for locating and mapping a catheter in intracardiac operations without using x-ray fluoroscopy, thereby limiting x-ray radiation exposure to the physician and patient, and also, without using ultrasound or MRI imaging.

It is yet another object of the present invention to provide an apparatus and method for locating and mapping a catheter in intracardiac operations that provides high accuracy in locating a catheter in the inspected organ.

It is a further object of the present invention to provide an apparatus and method for locating and mapping a catheter in intracardiac operations that provides highly accurate and reliable information for composing a three-dimensional images of the inspected organ.

It is a still further object of the present invention to provide an apparatus and method for locating and mapping a catheter in intracardiac operations that provides accurate and reliable information to enable the physician to minimize ablation damage to the surrounding tissues.

It is a yet further object of the present invention to provide an apparatus and method for locating and mapping a catheter in intracardiac operations that uses a Hall effect solid state magnetic field sensor with an ablating distal tip as part of a catheter, along with electrocardiogram (ECG) sensing electrodes.

It is another object of the present invention to provide an apparatus and method for locating and mapping a catheter in intracardiac operations in which the catheter is low cost and disposable.

It is still another object of the present invention to provide an apparatus and method for locating and mapping a catheter in intracardiac operations that is easy and economical to make and use.

In accordance with an aspect of the present invention, an apparatus for locating and mapping a catheter in body invasive operations, includes a device for creating a directional magnetic field that revolves 360 degrees through a person's body in correspondence to a specific organ in the person's body; a catheter for insertion into the organ, the catheter including a first sensing group including three sensors facing in mutually orthogonal directions and which detect a strength of the revolving magnetic field; and a central processing unit for computing and determining a location of the catheter in relation to the organ in response to the detected strength of the revolving magnetic field by the sensors of the first sensing group and an angular position of the directional magnetic field.

Specifically, the device for creating the directional magnetic field includes a north pole magnet generator, a south pole magnet generator, and a frame for positioning the north and south pole magnet generators on opposite sides of the person's body in correspondence to the specific organ in the person's body. Preferably, the north pole magnet generator includes a permanent magnet with a north pole face and the south pole magnet generator includes a permanent magnet with a south pole face, and a revolving assembly revolves the north and south pole magnetic generators in synchronism and in alignment with each other.

In this regard, the revolving assembly includes a first motor assembly for revolving the north pole magnetic generator and a second motor assembly for revolving the south pole magnetic generator. Each motor assembly includes a rotatable motor shaft and a front plate mounted on the motor shaft, the north pole magnet generator includes a permanent magnet with a north pole face and is mounted to a peripheral portion of the respective front plate, and the south pole magnet generator includes a permanent magnet with a south pole face and is mounted to a peripheral portion of the respective front plate.

The frame for positioning the north and south pole magnet generators includes a U-shaped support made from a ferrous magnetic material and having two parallel, spaced apart legs connected together by a connecting leg, with the north pole magnet generator mounted at a free end of one the leg and the south pole magnet generator mounted at a free end of the other the leg. The U-shaped support is hinged at the connecting leg so that the free ends can be moved toward and away from each other.

A position detector detects the angular position of the directional magnetic field. The position detector includes a plurality of position indicators on at least one front plate, and an indicator detection unit mounted to a fixed housing adjacent to the plurality of position indicators for detecting each position indicator passing by the indicator detector unit so as to produce an indication signal of speed and angular position of the permanent magnets, which is supplied to the central processing unit.

The catheter further includes a plurality of electrodes spaced along an outer wall thereof for detecting electric signals which run along a wall of the organ, and an ablation member at a tip of the catheter for burning out a wall of the organ.

The central processing unit also creates a three-dimensional image of the organ for display on a monitor in response to the determined locations of the catheter.

As to the sensors, there is also a second sensing group mounted on the catheter in axially spaced apart relation from the first sensing group, the second sensing group including three sensors which face in mutually orthogonal directions. Each sensor is preferably a solid state magnetic sensor.

In accordance with another aspect of the present invention, a method for locating and mapping a catheter in body invasive operations, includes the steps of creating a directional magnetic field that revolves 360 degrees through a person's body in correspondence to a specific organ in the person's body; inserting a catheter into the organ; detecting a strength of the revolving magnetic field by a first sensing group including three sensors facing in mutually orthogonal directions on the catheter; and determining a location of the catheter in relation to the organ in response to the strength of the revolving magnetic field detected by the sensors of the first sensing group and an angular position of the directional magnetic field.

The step of creating includes the step of positioning a north pole magnet generator and a south pole magnet generator on opposite sides of the person's body in correspondence to the specific organ in the person's body, wherein the north pole magnet generator includes a permanent magnet with a north pole face and the south pole magnet generator includes a permanent magnet with a south pole face, and then revolving each of the permanent magnets in synchronism and in alignment with each other.

In addition, the speed and angular position of the directional magnetic field are detected by a plurality of position indicators revolvable with the permanent magnets and an indicator detection unit mounted to a fixed housing adjacent to the plurality of position indicators by detecting each position indicator passing by the indicator detector unit so as to produce an indication signal of speed and position of the revolving permanent magnets. The indication signals are then supplied to the central processing unit which computes and determines the location of the catheter in relation to the organ in response thereto.

In addition, electric signals which run along a wall of the organ are detected by a plurality of electrodes spaced along an outer wall of the catheter.

After the detection operation, the catheter is accurately positioned in relation to the organ in response to previously determined locations and previously detected electrical signals which run along the wall of the organ, to find the occurrence of defective tissue of the organ, and the defective tissue is ablated by an ablation member at a tip of the catheter.

A three-dimensional image of the organ is also created for display on a monitor in response to the determined locations of the catheter.

Further, there is a second sensing group of three sensors which face in mutually orthogonal directions, mounted on the catheter in axially spaced relation to the first sensing group, and the step of detecting includes the step of detecting the strength of the revolving magnetic field occurs by the sensors of the first and second sensing groups.

The above and other objects, features and advantages of the present invention will become readily apparent from the following detailed description thereof which is to be read in connection with the accompanying drawings.

DETAILED DESCRIPTION

Figure 1:
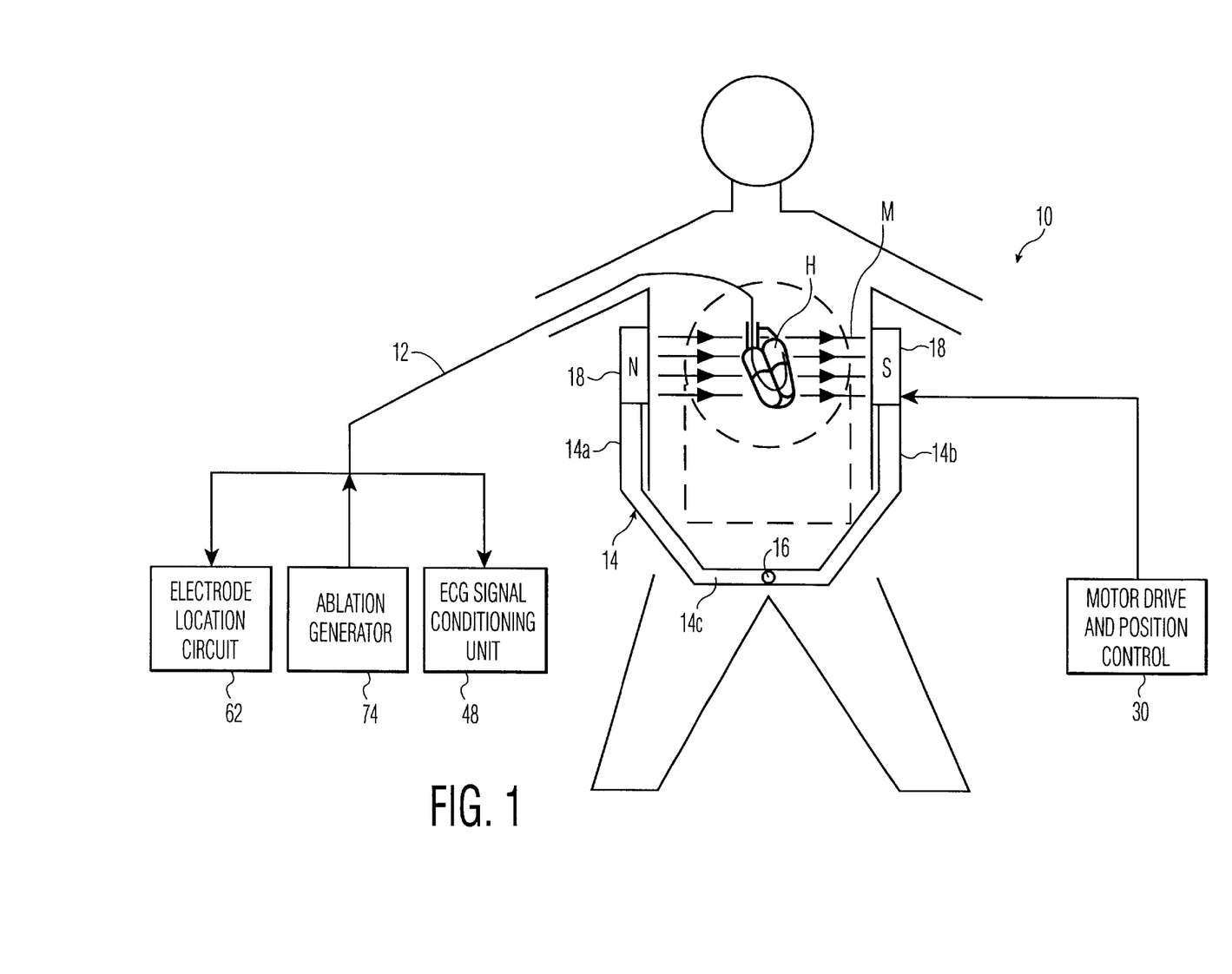
FIG. 1 is a schematic view of an apparatus for locating and mapping a catheter in intracardiac operations according to the present invention.

Referring to the drawings in detail, an apparatus 10 for locating and mapping a catheter 12 for use in intracardiac applications such as cardiac arrhythmia, ventricular tachycardia and other heart disorders, includes a U-shaped support 14 having first and second legs 14a and 14b that are connected at lower ends thereof by a connecting leg 14c. Connecting leg 14c includes a hinge 16 at its center so that the free ends of legs 14a and 14b can be moved away from each other to permit a patient to enter therebetween and toward each other so that the free ends are in contact, or substantially in contact, with opposite sides of the patient at the level of the patient's heart H, as shown in FIG. 1. The use of hinge 16 thereby allows use of the apparatus on different body sizes, and to compensate for mechanical changes in chest volume while the patient is breathing.

Figure 2:
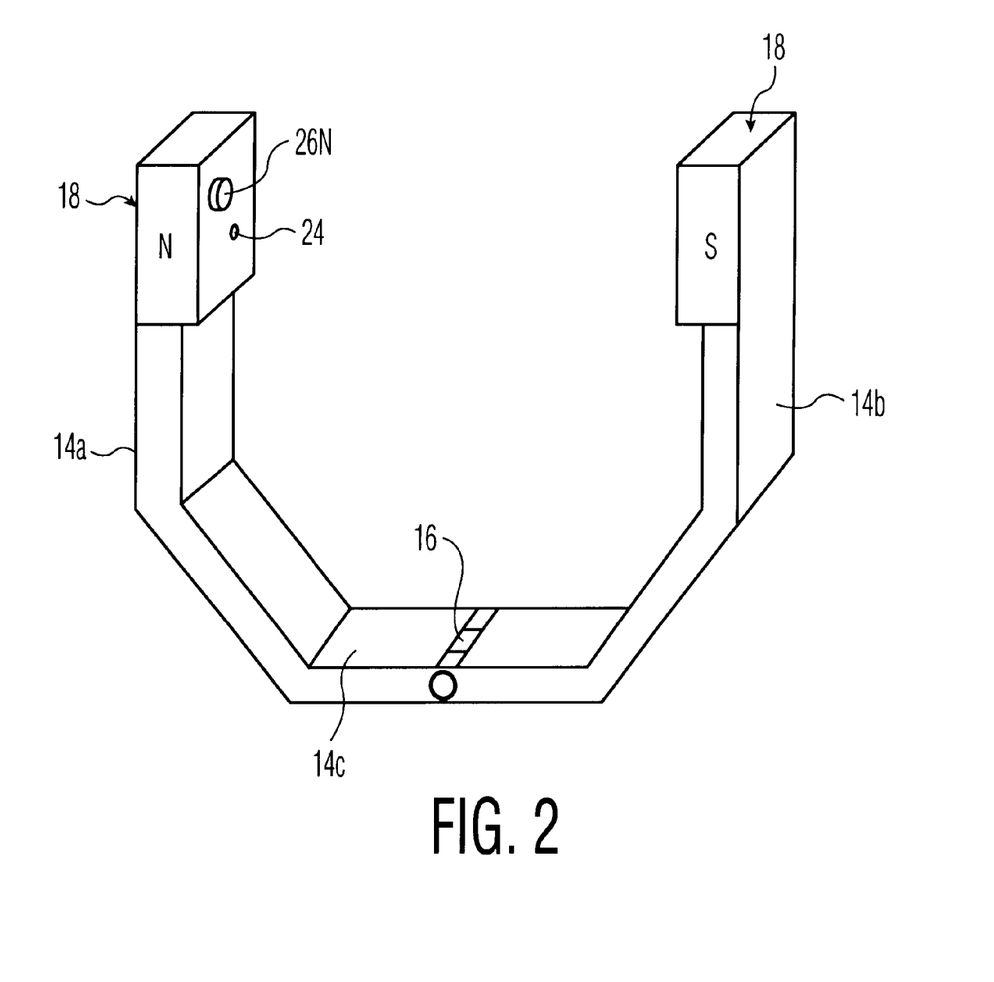
FIG. 2 is a perspective view of the U-shaped support.
Figure 3A:
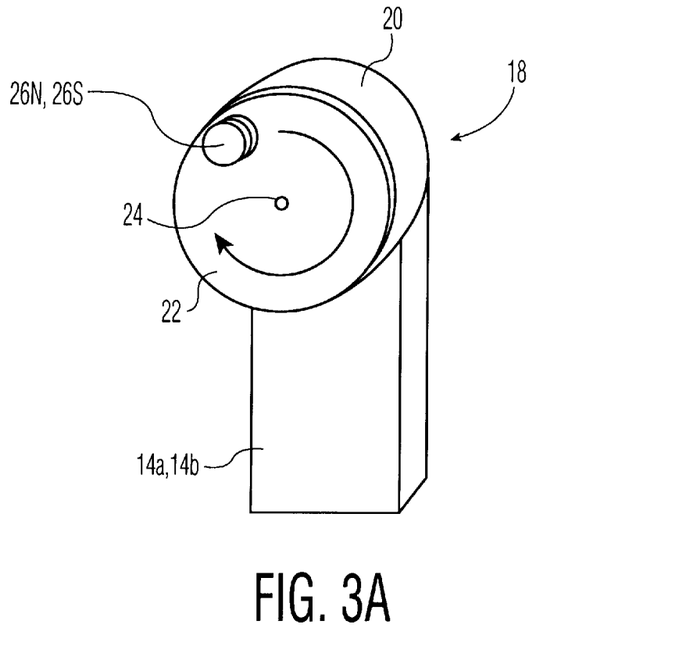
FIG. 3A is a perspective view of a portion of one leg of the U-shaped support with the revolving permanent magnet thereon.

A motor 18 is mounted to the free end of each leg 14a and 14b. Preferably, each motor 18 is a stepper motor whereby the position and speed of the motor can be controlled. Motor 18 is only shown schematically by its motor housing in FIGS. 1 and 2, although the actual housing 20 preferably takes the shape shown in FIG. 3A. In FIG. 3A, a circular front plate 22 covers the front opening of housing 20 and is mounted to the end of the motor shaft 24. Accordingly, front plate 22 rotates with motor shaft 24. A permanent magnet 26N or 26S is mounted at the periphery of each front plate 22 and is made from a ferrous magnetic material. Specifically, magnet 26N mounted to front plate 22 associated with leg 14a has a north pole face, while magnet 26S mounted to front plate 22 associated with leg 14b has a south pole face. As a result, a directional magnetic field is created between magnets 26N and 26S. Front plates 22 rotate in synchronism with each other and such that magnets 26N and 26S are always facing each other. As a result, a horizontal revolving magnetic field or flux M is generated through the patient at heart level, that is, across the heart. Motor shaft 24 can rotate at any suitable speed, such as up to 1,000 rpm. It is further noted that U-shaped support 14 is also made of a ferrous magnetic material so as to maintain the closed magnetic loop created by the revolving magnets 26N and 26S.

Figure 4:
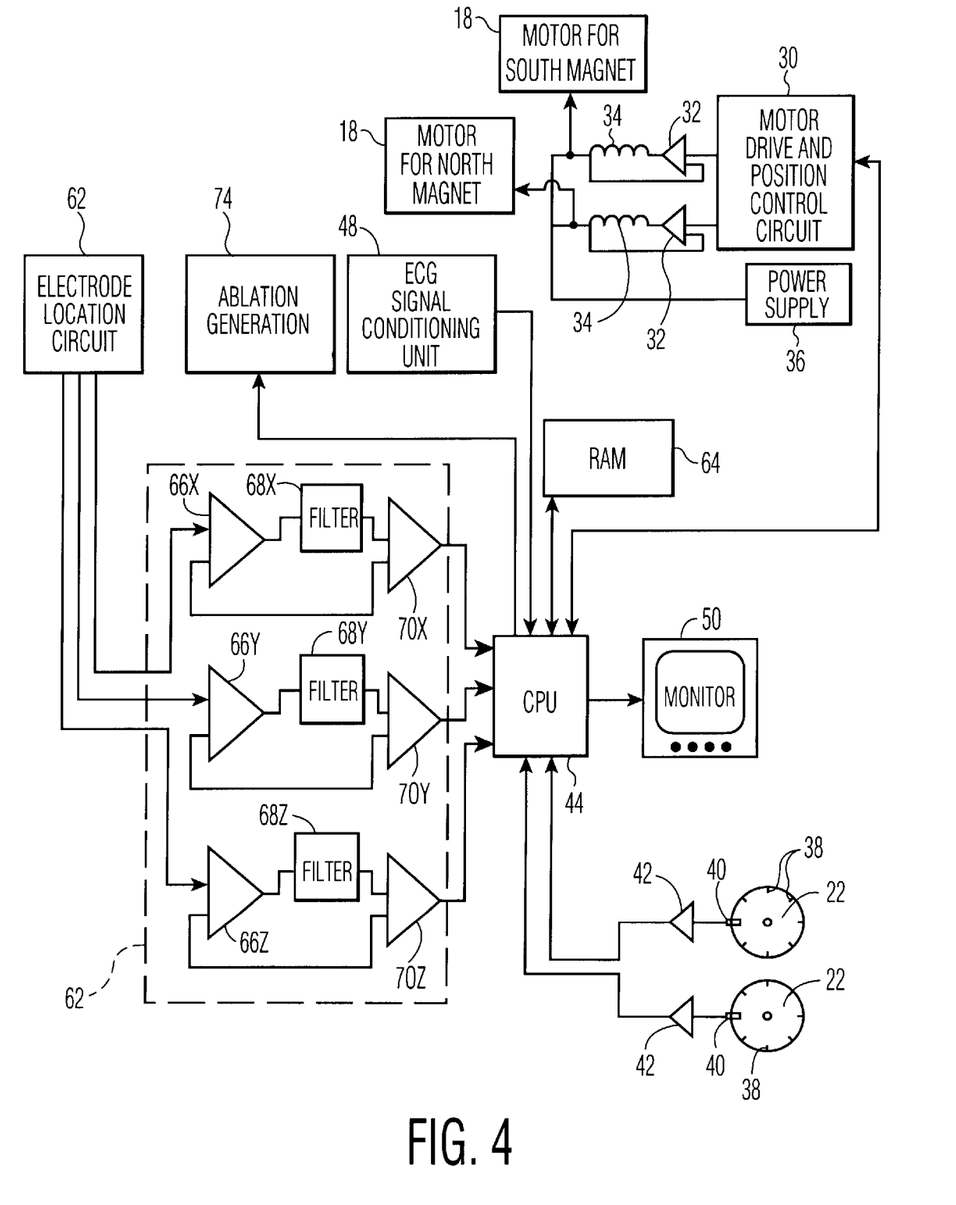
FIG. 4 is a block-circuit wiring diagram of the control circuitry of the apparatus.

As shown in FIG. 4, motors 18 are controlled by a motor drive and position control circuit 30 that supplies appropriate control signals for each motor 18 through an amplifier 32 and motor drive coil 34 in order to control the speed and angular position of motor shaft 24, and thereby of magnets 26N and 26S. A power supply 36 supplies power to motors 18 and motor drive and position control circuit 30 for this purpose.

An angular position and speed indicator is provided with each leg 14a and 14b. Specifically, each front plate 22 is provided with a plurality of position indicators 38 on the inner surface thereof, and an indicator detection unit 40 is mounted to each housing 20 at the open end thereof that is covered by the front plate 22. As a result, detection unit 40 detects each time that a position indicator 38 revolves therepast, and thereby provides an indication as to the speed and angular position of magnets 26N and 26S. Position indicators 38 and detection unit 40 can be any conventional devices, such as a photodetector for detection unit 40 and markings for position indicators 38, or any other suitable device.

The outputs from detection units 40 are supplied through amplifiers 42 to a central processing unit (CPU) 44, which analyzes the signals and determines the position and angular speed of front plate 22, and then sends appropriate correction signals to motor drive and position control circuit 30 in order to control the speed and angular position of magnets 26N and 26S.

According to the present invention, catheter 12 is inserted through blood vessels into heart H in order to detect defective tissue or lesions of the heart, and then to ablate the same. Thus, the magnetic field M is used to accurately detect the position of catheter 12 at all times and to use the coordinates of catheter 12 to provide an accurate and reliable three-dimensional plot of inner heart H for purposes of ablation.

Figure 5:
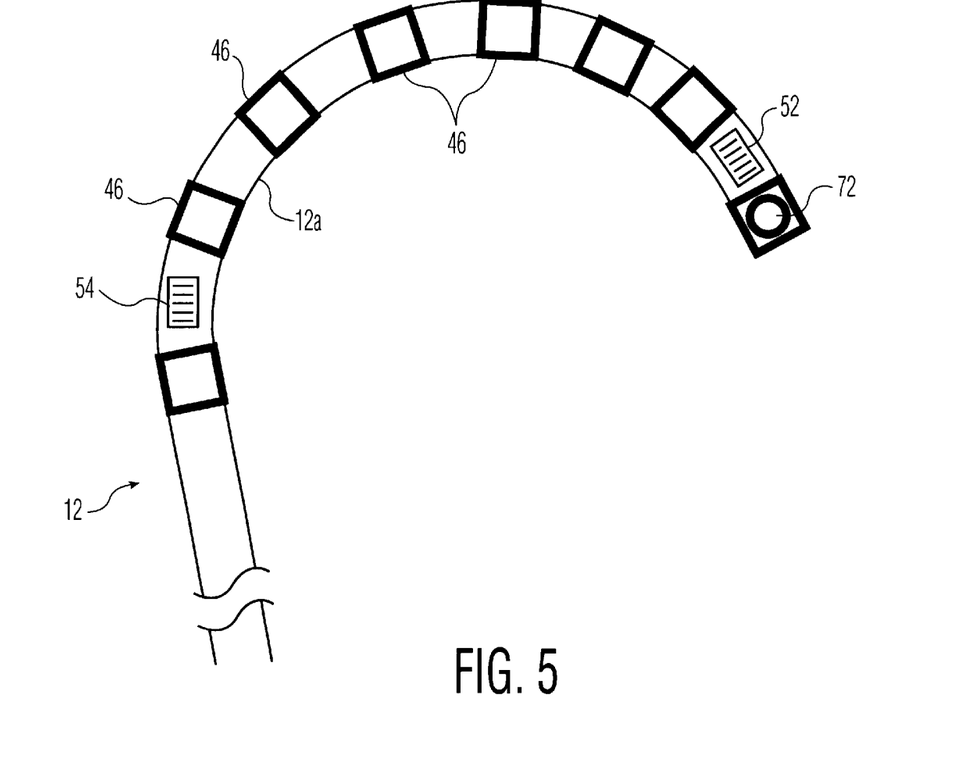
FIG. 5 is a plan view of the catheter.

As shown in FIG. 5, catheter 12 is made from a flexible tubular material, as is well known, and includes spaced metal ring ECG sensing electrodes 46 on the outside wall thereof which are individually and independently sensing the timed progression of the electrical signal along the heart wall. When ECG sensing electrodes 46 touch the inner wall of heart H at different locations, they detect the signals which stimulate the contraction of heart H and which run along the inner wall of heart H. Alternatively, stimulus signals can be supplied to heart H, and be detected by electrodes 46 of catheter 12. Further, a plurality of such catheters 12 can be provided at the same time in heart H for such measurement. The signals are received by an ECG signal conditioning unit 48 which, in turn, supplies the signals to CPU 44 for display. Based on this analysis, CPU 44 provides an indication in any suitable format on a monitor 50 of the measure of the electrical activity of heart H.

Figure 6:
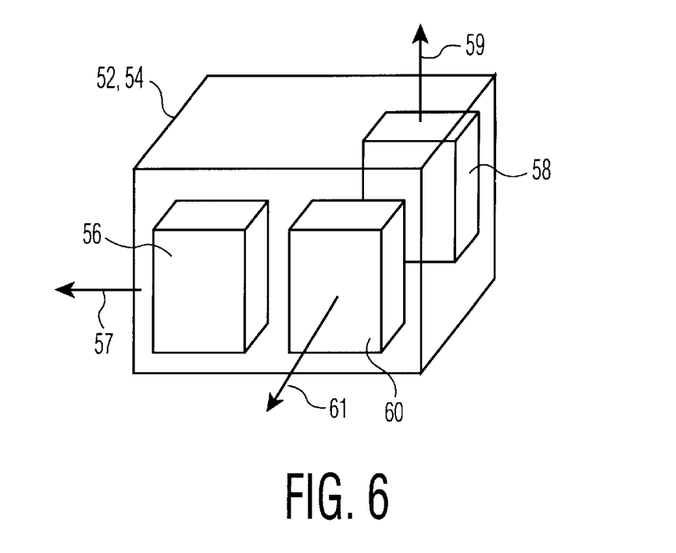
FIG. 6 is a perspective view of one magnetic sensor group of the catheter.

In addition, catheter 12 includes two spaced apart solid state Hall effect magnetic sensor groups 52 and 54. Magnetic sensor group 52 is located at the distal tip of catheter 12 to one side of sensing electrodes 46, while the other magnetic sensor group 54 is located at the other proximal side of sensing electrodes 46. Each sensor group 52 and 54 includes an X-axis or horizontal sensor 56 which senses a magnetic flux in an X-direction 57, a Y-axis or vertical sensor 58 which senses a magnetic flux in a Y-direction 59 and a Z-axis or depth sensor 60 which senses a magnetic flux in a Z-direction 61.

Preferably, each sensor 56, 58 and 60 is a solid state Hall effect magnetic sensor, which indicates changes in the electrical current of the sensor when approaching a magnetic field. An example of such a suitable three axis Hall effect sensor is one sold by F.W. Bell of Orlando, Fla. under Model No. BH-703. Similarly, the magnetic sensors can be of the type of giant magnetoresistive (GMR) sensors, for example, of the type sold by NVE, Nonvolatile Electronics, Inc. of Eden Prairie, Minnesota, or a resistive magnetic sensor. Such sensors can be produced in small size housings, as small as 0.05 inch by 0.05 inch substrates, which are sufficiently small to be implemented inside an intracardiac catheter.

Further, solid state sensors can pin-point a direction much better than with a coil. This is because of the sensing element which is very directive or linear. Also, solid state sensors can detect a stationary magnetic field, whereas inductors can only detect an alternating magnetic field. Thus, with the present invention, the magnets can be rotated in an incremental or stepped manner and then stopped for the purpose of taking a more prolonged measurement, for better resolution. All conventional systems use coils for creating a magnetic field and for measuring the intensity of the magnetic field. However, this suffers from the disadvantages discussed above. Further, the use of coils requires a much higher current, and it is difficult to reduce the size and place the coils in a catheter.

Electrical leads inside the tubing 12a of catheter 12, supply the necessary current to drive the sensors, which in turn, send electrical signals that are relative to the magnetic field strength and direction.

Figure 3B:
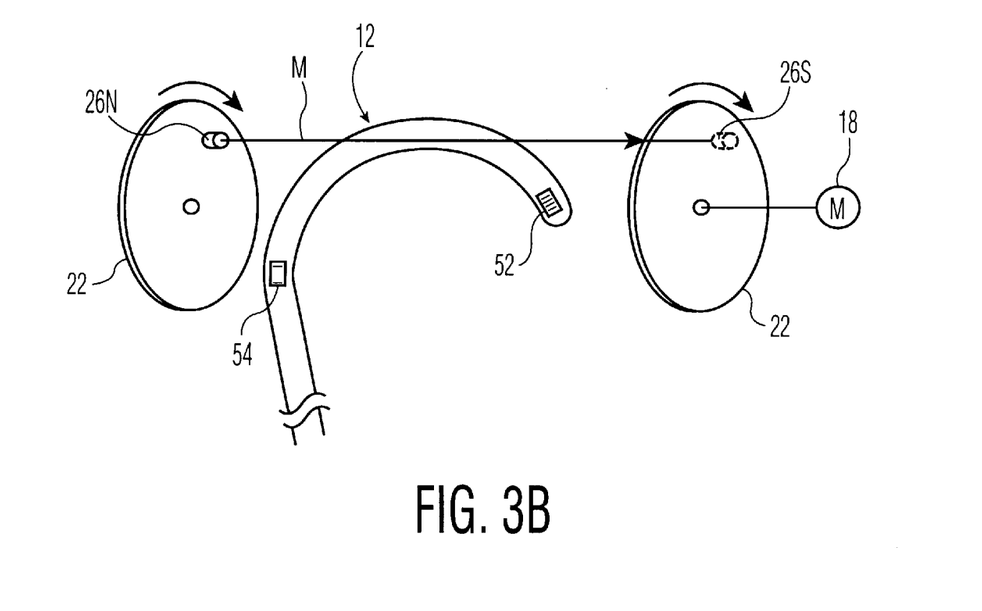
FIG. 3B is a schematic, perspective view showing the catheter in relation to the revolving magnetic field.

When catheter 12 is manipulated inside heart H, catheter 12 moves within the revolving magnetic flux area of magnetic field M. The closer a sensor is to the direct line between magnets 26N and 26S, the stronger the signal. Further, if a sensor is directed directly toward the line between magnets 26N and 26S, there is a stronger signal than if the sensor is turned away from this direct line. This will also indicate the orientation of catheter 12, depending upon whether an X-axis, Y-axis or Z-axis sensor produces a stronger signal. Thus, by providing two sensor groups 52 and 54, each with three orthogonal magnetic sensors 56, 58 and 60, CPU 44 can analyze and calculate the relative X, Y and Z orientation of catheter 12 with respect to main magnetic field M, even if catheter 12 becomes twisted or turned around.

The signals from sensor groups 52 and 54 are supplied to an electrode location circuit 62 which conditions the signals and supplies the conditioned signals to CPU 44. In response to the signals supplied from electrode location circuit 62 to CPU 44, and the signals supplied to CPU 44 from indicator detection units 40 as to the angular position and speed of magnets 26N and 26S, CPU 44 determines the coordinates and orientation of catheter 12 and supplies signals to monitor 50 to indicate this position and orientation of catheter 12. The beam positioning created by magnets 26N and 26S relative to magnetic sensor groups 52 and 54 allows CPU 44 to distinguish the proportional location of catheter 12 relative to the anatomy of heart H.

This is important for providing an indication as to the electrical signals traveling along the inner walls of heart H from electrodes 46. Because it is possible to determine the exact location of the defective tissue, ablation can occur with respect to accurately defined areas, so that only those areas of heart H which are necessary to be ablated are burned out, that is, avoiding burning out an area which is much larger than each area of defective tissue, as in the prior art.

In addition, CPU 44 stores each of these signals in a memory, such as a random access memory (RAM) 64, and can retrieve all of the signals to create a three-dimensional model of heart M on monitor 50 prior to ablation. By accurately mapping a three-dimensional image of heart H, the location of key nerves in heart H can be determined by the known location of such nerves in a conventional heart, so as to avoid burning out these key nerves. In other words, if a surgeon has a three-dimensional model of heart H from the sensors, the surgeon knows where the key nerves would normally occur on a heart and knows to stay away from these areas during the ablation operation. In addition, the three-dimensional mapping provides a pin-point location for the ablation.

As shown in FIG. 4, electrode location circuit 62 includes three input amplifiers 66X, 66Y and 66Z for amplifying the X-axis, Y-axis and Z-axis signals from magnetic sensors 56, 58 and 60 of magnetic sensor groups 52 and 54. The input signals from sensor group 52 can be input in a time displaced manner from the input signals from sensor group 54, or can be coded differently, in order to distinguish the signals. Alternatively, a separate electrode location circuit can be used for each sensor group 52 and 54. The output from each amplifier 66X, 66Y and 66Z is then supplied through band pass filters 68X, 68Y and 68Z, respectively, which condition the signals, and then through amplifiers 70X, 70Y and 70Z, respectively, to CPU 44.

It will be appreciated that the resolution of information regarding the position of catheter 12, as determined by the signals from magnetic sensors 56, 58 and 60, will be determined by the number of times during a single 360 degree revolution of magnets 26N and 26S that readings are taken. For example, a higher resolution is obtained if a reading is taken ever one degree, rather than every 10 degrees of revolution of magnetic field M.

A separate ablation catheter that also has the same magnetic sensor configuration built at its distal tip can be easily manipulated in the heart and be navigated to the ablation area based on traveling coordinates acquired from the magnetic sensing catheter.

Alternatively, the same catheter 12 can be provided with an ablation tip or heating element 72 at the distal end thereof. This is different from conventional applications in which multiple electrodes or catheters are provided for each application, that is, ECG monitoring and ablation. Thus, in this embodiment, the present invention provides an all-inclusive solution by providing ablation tip 72 on the same catheter as that used for ECG monitoring. Ablation tip 72 is connected to an RF ablation generator that provides the necessary energy to burn the defective tissue (ablation) on the heart wall. In this regard, magnetic sensor groups 52 and 54 provide the signals to CPU 44 for correctly locating catheter 12 in the ablation step.

Thus, upon insertion of catheter 12 into heart H, as shown in FIG. 1, apparatus 10 is activated. Some x-ray fluoroscopy may be used at the beginning of the operation in order to correctly position catheter 12 in heart H, and to mark a few basic reference points, but is not used thereafter. At this stage, permanent magnets 26N and 26S start to revolve by means of motors 18 at a steady and synchronized speed, and in alignment with each other. As a result, a directive revolving magnetic beam is created, which travels 360 degrees around a circle in relation to heart H, creating a cylindrical cage of magnetic beams that cross the heart in a 360 degree circle. Magnetic sensors 56, 58 and 60 of magnetic sensor groups 52 and 54 detect the magnetic field, and based on the position of the magnetic field, that is, the position of magnets 26N and 26S, and the strength of the magnetic field detected by each sensor, the position of catheter 12 can easily be determined. In this manner, an accurate three-dimensional model of heart H can be obtained, with accurate measurements of the electrical activity of heart H.

Then, after the three-dimensional model and the electrical activity of heart H have been determined, ablation occurs by either the same catheter 12 with ablation tip 72 or by a separate ablation catheter, which uses the same revolving magnetic field and the same magnetic sensors 56, 58 and 60 to accurately position catheter 12, and more particularly, ablation tip 72 thereof, at the correct pin-point location (defective tissue areas) for ablation. Further, only that area that needs to be burned out is ablated, thereby minimizing ablation damage to the surrounding tissues, in contrast to the prior art.

The above operation occurs without using extensive x-ray fluoroscopy, thereby limiting x-ray radiation exposure to the physician and patient.

It will be appreciated that, while the present invention has been discussed relative to an intracardiac operation, apparatus 10 can be used with any other bodily organ.

Having described a specific preferred embodiment of the invention with reference to the accompanying drawings, it will be appreciated that the present invention is not limited to that precise embodiment, and that various changes and modifications can be effected therein by one of ordinary skill in the art without departing from the scope or spirit of the invention as defined by the appended claims.

What is claimed is:

1. An apparatus for locating and mapping a catheter in body invasive operations, comprising:
   a device for creating a directional magnetic field, with the directional magnetic field revolving 360 degrees through a person's body in correspondence to a specific organ in the person's body, said device including:
   a north pole magnet generator,
   a south pole magnet generator, with the directional magnetic field being created by both the north and south pole magnetic generators and extending between said north pole magnet generator and said south pole magnet generator,
   a frame for positioning said north and south pole magnet generators on opposite sides of the person's body in correspondence to the specific organ in the person's body, and
   a revolving assembly for rotating said north and south pole magnet generators on said first and second opposite sides, respectively, in synchronism and in alignment with each other, in planes substantially transverse to said directional magnetic field such that said directional magnetic field traces a substantially cylindrical path during said rotation;
   a catheter for insertion into the organ, said catheter including a first sensing group including three sensors facing in mutually orthogonal directions and which detect a strength of said revolving magnetic field;
   a position detector for detecting an angular position of said directional magnetic field; and
   a central processing unit for computing and determining a location of said catheter in relation to said organ in response to said detected strength of said revolving magnetic field by said sensors of said first sensing group and the angular position of said directional magnetic field.

2. An apparatus according to claim 1, wherein said north pole magnet generator includes a permanent magnet with a north pole face and said south pole magnet generator includes a permanent magnet with a south pole face.

3. An apparatus for locating and mapping a catheter in body invasive operations, comprising:
   a device for creating a directional magnetic field, with the directional magnetic field revolving 360 degrees through a person's body in correspondence to a specific organ in the person's body, said device including:
   a north pole magnet generator,
   a south pole magnet generator,
   a frame for positioning said north and south pole magnet generators on opposite sides of the person's body in correspondence to the specific organ in the person's body, and
   a revolving assembly for revolving said north and south pole magnetic generators in synchronism and in alignment with each other, said revolving assembly including a first motor assembly for revolving said north pole magnetic generator and a second motor assembly for revolving said south pole magnetic generator;
   a catheter for insertion into the organ, said catheter including a first sensing group including three sensors facing in mutually orthogonal directions and which detect a strength of said revolving magnetic field;
   a position detector for detecting an angular position of said directional magnetic field; and
   a central processing unit for computing and determining a location of said catheter in relation to said organ in response to said detected strength of said revolving magnetic field by said sensors of said first sensing group and the angular position of said directional magnetic field.

4. An apparatus according to claim 3, wherein:
   each said motor assembly includes a rotatable motor shaft and a front plate mounted on said motor shaft,
   said north pole magnet generator includes a permanent magnet with a north pole face and is mounted to a peripheral portion of said respective front plate, and
   said south pole magnet generator includes a permanent magnet with a south pole face and is mounted to a peripheral portion of said respective front plate.

5. An apparatus according to claim 4, wherein said position detector includes a plurality of position indicators on at least one said front plate, and an indicator detection unit mounted to a fixed housing adjacent to said plurality of position indicators for detecting each position indicator passing by said indicator detector unit so as to produce an indication signal of speed and position of said permanent magnets, which is supplied to said central processing unit.

6. An apparatus for locating and mapping a catheter in body invasive operations, comprising:
   a device for creating a directional magnetic field, with the directional magnetic field revolving 360 dearees through a person's body in correspondence to a specific organ in the person's body, said device including:
   a north pole magnet generator,
   a south pole magnet generator, and
   a frame for positioning said north and south pole magnet generators on opposite sides of the person's body in correspondence to the specific organ in the person's body, said frame including a U-shaped support conducted at least from a material which includes a ferrous magnetic material and having two parallel, spaced apart legs connected together by a connecting leg, with said north pole magnet generator mounted at a free end of one said leg and the south pole magnet generator mounted at a free end of the other said leg;
   a catheter for insertion into the organ, said catheter including a first sensing group including three sensors facing in mutually orthogonal directions and which detect a strength of said revolving magnetic field;

a position detector for detecting an angular position of said directional magnetic field; and a central processing unit for computing and determining a location of said catheter in relation to said organ in response to said detected strength of said revolving magnetic field by said sensors of said first sensing group and the angular position of said directional magnetic field.

7. An apparatus according to claim 6, wherein said U-shaped support is hinged at said connecting leg so that said free ends can be moved toward and away from each other.

8. An apparatus according to claim 1, wherein said catheter further includes a plurality of electrodes spaced along an outer wall thereof for detecting electric signals which run along a wall of said organ.

9. An apparatus according to claim 1, wherein said catheter further includes an ablation member at a tip of said catheter for burning out a wall of said organ.

10. An apparatus according to claim 1, wherein said central processing unit creates a three-dimensional image of said organ for display on a monitor in response to said determined locations of said catheter.

11. An apparatus according to claim 1, further including a second sensing group mounted on said catheter in axially spaced apart relation from said first sensing group, said second sensing group including three sensors which face in mutually orthogonal directions.

12. An apparatus according to claim 1, wherein each said sensor is a solid state magnetic sensor.

13. A method for locating and mapping a catheter in body invasive operations, comprising the steps of:

creating a directional magnetic field that revolves through 360 degrees through a person's body in correspondence to a specific organ in the person's body, said step of creating including the steps of:

positioning a north pole magnet generator on a first side of the person's body in correspondence to the specific organ in the person's body, positioning a south pole magnet generator on a second side of the person's body in correspondence to the specific organ in the person's body, with the directional magnetic field being created by both the north and south pole magnetic generators and extending between said north pole magnet generator and said south pole magnet generator, revolving said north and south pole magnet generators on said first and second opposite sides, respectively, in synchronism and in alignment with each other, in planes substantially transverse to said directional magnetic field such that said directional magnetic field traces a substantially cylindrical path during said rotation;

inserting a catheter into the organ;

detecting a strength of said revolving magnetic field by a first sensing group including three sensors facing in mutually orthogonal directions on said catheter;

detecting an angular position of said directional magnetic field; and determining a location of said catheter in relation to said organ in response to said strength of said revolving magnetic field detected by said sensors of said first sensing group and the angular position of said directional magnetic field.

14. A method according to claim 13, wherein said north pole magnet generator includes a permanent magnet with a north pole face and said south pole magnet generator includes a permanent magnet with a south pole face, and said step of creating includes the step of revolving each of said permanent magnets in synchronism and in alignment with each other.

15. A method according to claim 14, further including the steps of:

detecting the speed and angular position of said directional magnetic field by a plurality of position indicators revolvable with said permanent magnets and an indicator detection unit mounted to a fixed housing adjacent to said plurality of position indicators by detecting each position indicator passing by said indicator detector unit so as to produce an indication signal of speed and position of said permanent magnets, supplying said indication signals to a central processing unit which determines the location of said catheter in relation to said organ.

16. A method according to claim 13, further including the step of detecting electric signals which run along a wall of said organ by a plurality of electrodes spaced along an outer wall of said catheter.

17. A method according to claim 16, further including the steps of:

accurately positioning said catheter in relation to said organ in response to the location which was previously determined in said step of determining and in response to the electrical signals which were previously detected and which run along the wall of said organ, to find an occurrence of defective tissue of said organ, and ablating said defective tissue by an ablation member at a tip of said catheter.

18. A method according to claim 13, further comprising the step of creating a three-dimensional image of said organ for display on a monitor in response to said determined locations of said catheter.

19. A method according to claim 13, wherein there is a second sensing group mounted on said catheter in axially spaced relation to said first sensing group, and said step of detecting includes the step of detecting the strength of said revolving magnetic field by the sensors of said first and second sensing groups.

20. A method according to claim 13, wherein each said sensor is a solid state magnetic sensor.

* * * * *